United States Patent
Pavento et al.

(10) Patent No.: US 9,271,836 B2
(45) Date of Patent: Mar. 1, 2016

(54) NUBBED PLATE

(75) Inventors: Nicholas Pavento, North Attleboro, MA (US); John Riley Hawkins, Cumberland, RI (US); Sheryl Frank, Lakeville, MA (US); Douglas Raymond, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 497 days.

(21) Appl. No.: 13/413,264

(22) Filed: Mar. 6, 2012

(65) Prior Publication Data
US 2013/0238095 A1    Sep. 12, 2013

(51) Int. Cl.
*A61F 2/44*     (2006.01)
*A61F 2/30*     (2006.01)
(Continued)

(52) U.S. Cl.
CPC ......... *A61F 2/30744* (2013.01); *A61B 17/7059* (2013.01); *A61F 2/442* (2013.01); *A61F 2/4455* (2013.01); *A61F 2/30965* (2013.01); *A61F 2/447* (2013.01); *A61F 2/4465* (2013.01); *A61F 2002/2817* (2013.01); *A61F 2002/2835* (2013.01); *A61F 2002/305* (2013.01); *A61F 2002/30378* (2013.01); *A61F 2002/30482* (2013.01); *A61F 2002/30578* (2013.01); *A61F 2002/30596* (2013.01); *A61F 2002/30604* (2013.01); *A61F 2002/30607* (2013.01); *A61F 2002/30616* (2013.01); *A61F 2002/30774* (2013.01); *A61F 2002/30784* (2013.01); *A61F 2002/30785* (2013.01); *A61F 2002/30787* (2013.01); *A61F 2002/30836* (2013.01); *A61F 2002/30843* (2013.01); *A61F 2002/4475* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01); *A61F 2310/00053* (2013.01); *A61F 2310/00101* (2013.01); *A61F 2310/00161* (2013.01);
(Continued)

(58) Field of Classification Search
CPC ....... A61F 2/44; A61F 2/4425; A61F 2/4435; A61F 2/447; A61F 2/4475
USPC ............ 623/17.11–17.16; 606/86 A, 99, 100, 606/280–299
See application file for complete search history.

(56) References Cited

U.S. PATENT DOCUMENTS 5,755,796 A * 5/1998 Ibo et al. .................... 623/17.16
6,156,037 A * 12/2000 LeHuec et al. ................ 606/247
(Continued)

FOREIGN PATENT DOCUMENTS

WO    WO 2011/080535 A1    7/2011

OTHER PUBLICATIONS

International Preliminary Report on Patentability, International Application No. PCT/US2013/029026, date of mailing Sep. 9, 2014, 10 pages.
(Continued)

*Primary Examiner* — Christian Sevilla
*Assistant Examiner* — Eric S Gibson
(74) *Attorney, Agent, or Firm* — Raymond N. Scott, Jr.

(57) ABSTRACT

A separate nub component between the plate and an intervertebral fusion cage, wherein the nub is attached to the plate. The nub lessens the undesired pivotal movement of the plate. It is believed that when the nub fits snugly between the endplates of the adjacent vertebral bodies, it acts as a stop against the undesired pivotal movement of the plate.

17 Claims, 7 Drawing Sheets

(51) Int. Cl.
*A61B 17/70* (2006.01)
*A61F 2/28* (2006.01)

(52) U.S. Cl.
CPC ............... *A61F 2310/00179* (2013.01); *A61F 2310/00203* (2013.01); *A61F 2310/00239* (2013.01); *A61F 2310/00359* (2013.01); *A61F 2310/00407* (2013.01)

(56) References Cited

U.S. PATENT DOCUMENTS

| | | | |
|---|---|---|---|
| 6,432,106 B1 | 8/2002 | Fraser | |
| 6,508,818 B2 * | 1/2003 | Steiner et al. | 606/71 |
| 7,112,222 B2 | 9/2006 | Fraser et al. | |
| 7,594,931 B2 | 9/2009 | Louis et al. | |
| 7,887,595 B1 | 2/2011 | Pimenta | |
| 8,216,312 B2 * | 7/2012 | Gray | 623/17.11 |
| 8,357,200 B2 * | 1/2013 | Adl | 623/17.14 |
| 8,454,694 B2 * | 6/2013 | Armstrong et al. | 623/17.11 |
| 8,480,747 B2 | 7/2013 | Melkent et al. | |
| 8,562,651 B2 | 10/2013 | Metcalf et al. | |
| 8,690,948 B2 * | 4/2014 | Armstrong et al. | 623/17.16 |
| 8,758,439 B2 * | 6/2014 | Linares | 623/17.11 |
| 2002/0156475 A1 | 10/2002 | Lerch et al. | |
| 2004/0193269 A1 | 9/2004 | Fraser et al. | |
| 2007/0049941 A1 | 3/2007 | Thramann | |
| 2007/0055252 A1 | 3/2007 | Blain et al. | |
| 2007/0213820 A1 | 9/2007 | Magerl et al. | |
| 2007/0270965 A1 | 11/2007 | Ferguson | |
| 2008/0051890 A1 | 2/2008 | Waugh et al. | |
| 2008/0183294 A1 * | 7/2008 | Adl | 623/17.16 |
| 2009/0326580 A1 * | 12/2009 | Anderson et al. | 606/246 |
| 2010/0004747 A1 | 1/2010 | Lin | |
| 2010/0249935 A1 | 9/2010 | Slivka et al. | |
| 2010/0312345 A1 | 12/2010 | Duffield et al. | |
| 2011/0009908 A1 * | 1/2011 | Ferguson | 606/279 |
| 2011/0184415 A1 | 7/2011 | Anderson et al. | |
| 2011/0190892 A1 * | 8/2011 | Kirschman | 623/17.16 |
| 2011/0202136 A1 * | 8/2011 | Brittan et al. | 623/17.16 |
| 2012/0041559 A1 * | 2/2012 | Melkent et al. | 623/17.11 |
| 2012/0150303 A1 * | 6/2012 | Linares | 623/17.16 |
| 2013/0166027 A1 * | 6/2013 | Bellas | 623/17.16 |
| 2013/0238095 A1 * | 9/2013 | Pavento et al. | 623/17.16 |
| 2013/0345813 A1 * | 12/2013 | Frank et al. | 623/17.16 |
| 2014/0156009 A1 * | 6/2014 | Armstrong et al. | 623/17.16 |
| 2014/0172103 A1 * | 6/2014 | O'Neil et al. | 623/17.16 |

OTHER PUBLICATIONS

International Search Report, International Application No. PCT/US2013/029026, date of mailing May 23, 2013.
PCT Written Opinion of the International Searching Authority, International Application No. PCT/US2013/029026, date of mailing May 23, 2013, 9 pages.
Supplemental European Search Report, International Application No. EP 13757720, date of mailing Oct. 1, 2015, 6 pages.

* cited by examiner

1

NUBBED PLATE

BACKGROUND OF THE INVENTION

A lateral access approach is frequently selected to deliver intervertebral fusion cages to the lumbar spine. Compared to conventional anterior or posterior approaches to the lumbar spine, the lateral approach is thought to minimize posterior and/or anterior tissue damage as well as reduce surgery time, associated blood loss, vascular damage and infection risk.

In general, it is known in the art to mount a laterally-placed fusion cage with a plate that secures to the sides of adjacent vertebral bodies. This plate attaches to a side of each vertebral body adjacent the operative disc space. The primary purpose of the plate is to reduce the patient's ability to undergo excessive extension, thereby eliminating the need for the surgeon to implant posterior fixation.

U.S. Pat. No. 7,594,931 (Louis) discloses an intervertebral arthrodesis implant for insertion in an intervertebral space separating opposite faces of two adjacent vertebrae. The implant has a ring-shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebral faces.

PCT Published Patent Application WO2011-080535 (Dinville) discloses anchoring devices, anchoring systems for intervertebral implants, intervertebral implants, and instruments and methods for implanting the implants. In preferred configurations, these various objects share the feature of comprising or cooperating with an anchoring device having a body comprising at least one curved plate elongated along a longitudinal axis. The plate is designed to be inserted through a passage crossing at least a part of the implant in order to penetrate into at least one vertebral endplate and attach this implant onto this vertebral endplate by means of at least one stop retaining the implant. The body of the anchoring device comprises at least one longitudinal rib on at least a part of at least one of its faces, the rib being designed to cooperate with a groove made in a passage of implant.

In one type of intervertebral device suited for the lateral approach, the fusion cage is mounted with a plate that secures the cage to the adjacent vertebral bodies. In particular, US Published Patent Application 2010-0004747 (Lin) discloses a spinal fixation device comprising a trans-vertebral and intra-vertebral plate and a rectangular cage with a slot for the plate for neutralizing intervertebral movement in spinal interbody fusion. The rectangular cage with a vertical or oblique slot is inserted into the intervertebral space from the lateral or anterior side of the spinal column. The plate is then inserted through the slot of the cage and hammered into and buried inside the two adjacent vertebral bodies to achieve three-dimensional intervertebral fixation.

U.S. Pat. No. 6,432,106 (Fraser I) discloses a spinal fixation assembly includes a fusion cage to which a plate is mated. The plate is configured to receive, retain and orient bone screws.

U.S. Pat. No. 7,112,222 (Fraser II) discloses one type of prior art device that combines a cage with a plate, so that the cage is integrally bound to the plate. A representative side view of this assembly is shown in FIG. 14.

U.S. Pat. No. 7,112,222 (Fraser II) further discloses a spinal fixation assembly is provided including a fusion cage with posterior, anterior, superior, and inferior faces, and a plate having at least one aperture for receiving a bone screw and having a mating element adapted to slidably engage and mate to the anterior face of the fusion cage. The cage is adapted to be positioned between adjacent vertebrae, and the plate is effective to mate to the cage and to receive one or more bone screws to fasten the plate and secure the fusion cage to the adjacent vertebrae.

US Published Patent Application US 2011-0184415 discloses (Anderson) discloses a bone stabilization system is provided having a plate with a top and bottom surface and a hole therethrough extending along a longitudinal axis. An annular groove in the top surface encircles the axis and defines outer facing sides of a plurality of spring members integral to the plate. A plurality of slots define sides of the spring members the inward facing side of the spring members form the upper portion of the hole, which includes a first spherical portion. A fastener with a spherical portion on the fastener head extends into the hole with the spring members urged apart to allow the head to pass but restraining removal until the resistance provide by the spring members is overcome.

US Published Patent Application US 2007-0049941 discloses (Thramann) discloses a spinal fusion plate includes a means to support an adjacent vertebral segment to inhibit the adjacent vertebral segment from further degeneration. The means to support includes an attachment to an associated artificial disc or nucleus replacement, an extension, or an attachment to a bone anchor. In each case, the attachment is moveable in relation to the fusion plate to allow flexion and extension.

U.S. Pat. No. 7,887,595 (Pimenta) discloses a spinal fusion implant of non-bone construction to be introduced into an intervertebral disc space for the promotion of spinal fusion.

SUMMARY OF THE INVENTION

It has been observed by the present inventors that simply attaching a plate component against the trailing end of a lateral cage only imperfectly arrests the extension-like movement of the patient's spine. Rather, it was noticed that there was some anterior-posterior pivoting of the plate about the screw that connected the plate to the cage. See FIG. 18.

Therefore, it is an object of the present invention to provide a cage-plate assembly having a reduced ability to pivot.

In accordance with the present invention, the present inventors found that adding a separate nub component between the plate and cage, wherein the nub is attached to the plate, lessens the undesired pivotal movement of the plate. It is believed that when the nub fits snugly between the endplates of the adjacent vertebral bodies, it acts as a stop against the undesired pivotal movement of the plate.

Therefore, in accordance with the present invention, there is provided an intervertebral fusion device comprising:
 a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate;
 b) a bone plate comprising upper and lower holes,
 c) a separate nub component interposed between the bone plate and the trailing wall of the cage.

DETAILED DESCRIPTION OF THE INVENTION

Figure 1:
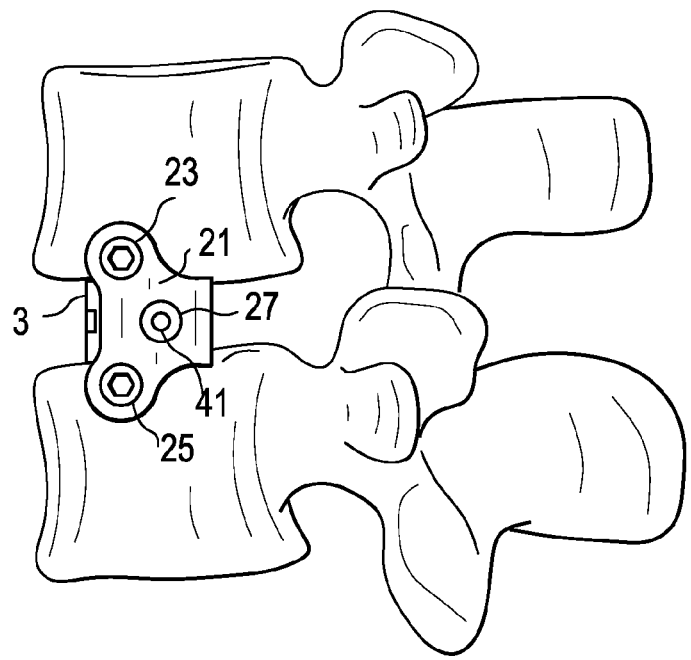
FIG. 1 shows a side view of a device of the present invention attached to sidewalls of adjacent vertebral bodies.
Figure 2:
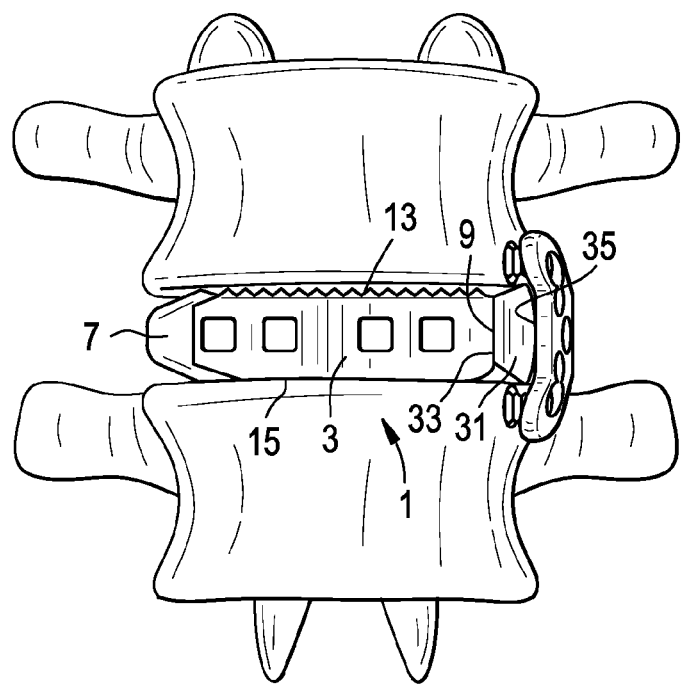
FIG. 2 shows a front view of a device of the present invention attached to sidewalls of adjacent vertebral bodies.

Now referring to FIGS. 1-6, there is provided an intervertebral fusion device comprising:
- a) an intervertebral fusion cage 1 having an anterior wall 3, a posterior wall 5, a leading wall 7 and a trailing wall 9 connecting the anterior and posterior walls to form a central vertical throughhole 11, an upper surface 13 adapted for gripping an upper endplate and a lower surface 15 adapted for gripping a lower endplate;
- b) a bone plate 21 comprising an upper hole 23, a lower hole 25, and a central hole 27 disposed substantially between the first and second holes,
- c) a nub 31 interposed between the bone plate and the trailing wall of the cage, the nub comprising:
    - i) a first wall 33 contacting the trailing wall of the cage,
    - ii) a second wall 35 contacting the bone plate,
    - iii) a threaded throughhole 37 extending from the first wall to the second wall, and
- d) a threaded post 41 received in the throughhole of the nub and passing through the central hole of the bone plate.

In some embodiments, the assembly has a polyaxial joint. It is believed that the inclusion of this polyaxial joint is very advantageous to the performance of the device. It has been noticed that typical variations in human physiology often result in a situation in which the sidewalls of the adjacent vertebrae that hold the plate are not coplanar with each other. Rather, one sidewall often extends out farther than its adjacent sidewall. Thus, when a conventional cage-plate assembly (in which the plate is rigidly attached to the cage in a perpendicular relationship) is used on a typical functional spinal unit, the lack of a coplanar relationship in the vertebral sidewalls leads to a fixation situation in which only one of the vertebral sidewalls will actually contact the plate. This asymmetrical contact undesirably leads to stress concentration and poor distribution of biomechanical forces (as one screw is loaded more), leading to bony fracture.

It is believed that a polyaxial joint in the cage-plate assembly alleviates these concerns. When the cage-plate assembly of the present invention is used on a typical functional spinal unit lacking coplanar vertebral sidewalls, the plate can be polyaxially adjusted about the cage until it contacts each of the sidewalls and then locked at that desired angle. This produces a fixation in which asymmetrical contact is eliminated.

Therefore, in accordance with the present invention, there is provided an intervertebral fusion device comprising:
- a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate, the upper and lower surface defining a cage height;
- b) a bone plate comprising a bone contacting surface, and outer surface, upper and lower holes passing from the bone-contacting surface to the outer surface, and a projection extending distally from the bone contacting surface and having a height, wherein the bone plate is connected to the trailing wall of the cage via a polyaxial connection.

Also in accordance with the present invention, there is provided an assembly device for fusing a disc space, comprising:
- a) a bone plate comprising a bone-contacting inner surface, an outer surface, upper and lower holes, a central hole, each hole passing from the outer surface to the inner surface,
- b) an intervertebral component comprising:
    - i) a first wall facing the disc space,
    - ii) a second wall contacting the inner surface of the bone plate,
- c) first and second bone anchors passing through the upper and lower holes of the bone plate, wherein the bone plate forms a polyaxial joint with the intervertebral component.

Figure 7:
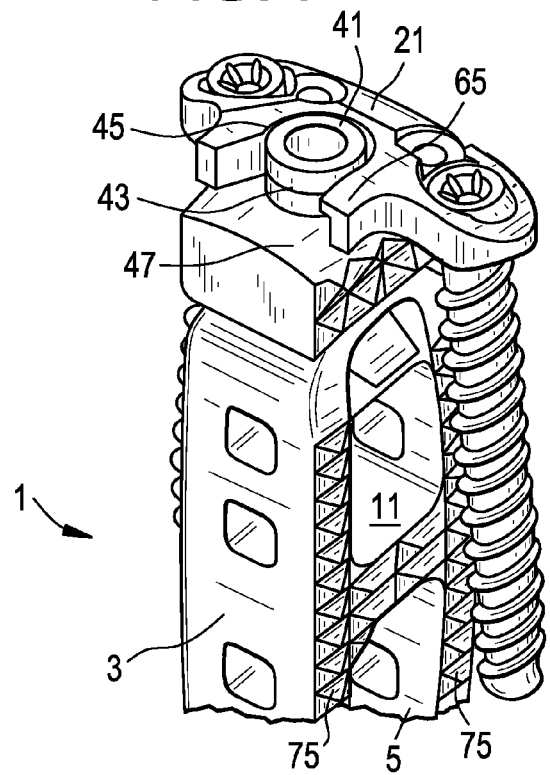
FIG. 7 discloses a perspective view of a first embodiment of a polyaxial assembly of the present invention.
Figure 8:
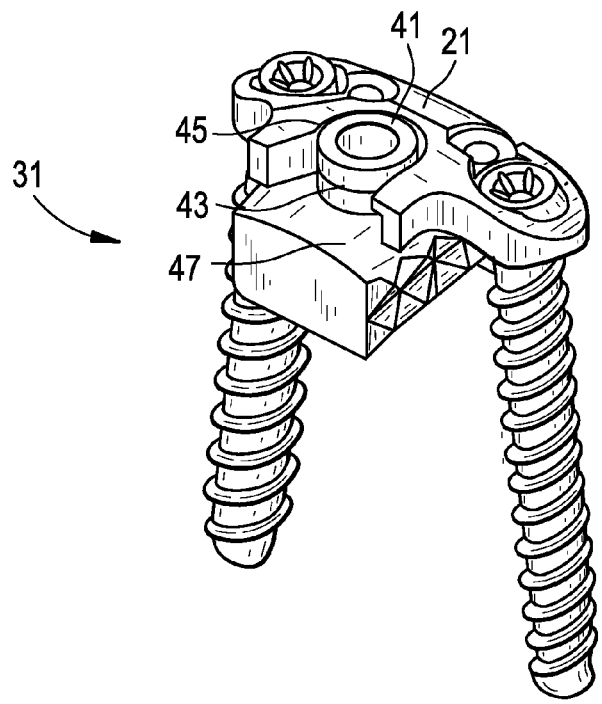
FIG. 8 discloses a perspective view of the plate and nub components of the first embodiment of a polyaxial assembly of the present invention.
Figure 10:
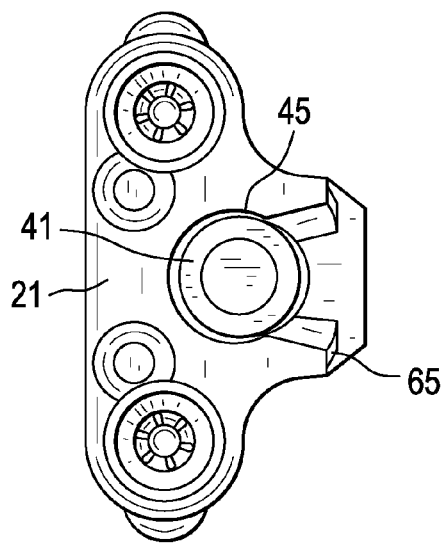
FIG. 10 shows a top view of the first embodiment of a polyaxial assembly of the present invention.

In a first polyaxial embodiment, and now referring to FIGS. 7, 8 and 10, the proximal head of the post comprises a spherical surface 43. This spherical surface can form a polyaxial joint with a mating spherical surface 45 formed in the central hole of the plate. Again, the polyaxial connection is advantageous for adjusting the orientation of the plate so that it evenly contacts both sidewalls of the adjacent vertebral bodies. Once the proper angulation is found, the post may be further threadably tightened into the nub to lock the desired angle.

Therefore, in accordance with the present invention, there is provided an interbody device for fusing a disc space, comprising:
- a) a bone plate comprising a bone contacting inner surface, an outer surface, upper and lower holes, a central hole having a spherical surface thereon, each hole passing from the outer surface to the inner surface,
- b) an intervertebral component comprising:
    - i) a first wall facing the disc space,
    - ii) a second wall contacting the inner surface of the bone plate,
    - iii) a threaded throughhole extending from the first wall to the second wall, c) first and second bone anchors passing through the upper and lower holes of the bone plate,
d) a post having a proximal spherical head and a distal threaded shaft, wherein the inner surface of the bone plate contacts the second wall of the intervertebral component, wherein the central hole of the bone plate and the threaded throughhole of the intervertebral component align, wherein the distal threaded shaft of the post is threadably received in the threaded throughhole of the nub, and wherein the proximal spherical head of the post is received in the spherical surface of the central hole of the bone plate to form a polyaxial joint).

Now referring to FIGS. 7-10, in some embodiments in which the plate and post form a polyaxial joint, the second wall of the nub (which contacts the bone plate) has a convex surface 47. This convex surface is useful in the polyaxial joint embodiments of the present invention because it accommodates more tilting of the plate with respect to the nub while maintaining the joint.

Likewise, in some embodiments in which the plate and post form a polyaxial joint, the inner surface of the bone plate has a concave surface 49. This concave surface is useful in the polyaxial joint embodiments in which the second wall of the nub is convex because it accommodates more tilting of the plate with respect to the nub while maintaining the joint.

Figure 9:
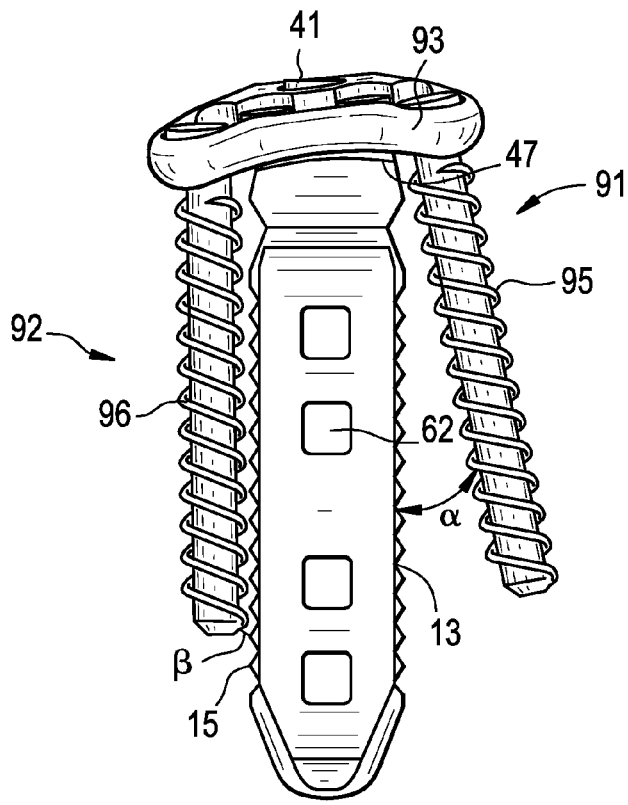
FIG. 9 shows a side view of the first embodiment of a polyaxial assembly of the present invention.

In some embodiments, and now referring to FIG. 9, the shaft 95 of the upper bone anchor 91 and the upper surface 13 of the cage define a first angle $\alpha$, the shaft 96 of the lower bone anchor 92 and the lower surface 15 of the cage define a second angle $\beta$, and the first angle $\alpha$ is not equal to second angle $\beta$. This condition occurs when a polyaxial joint is created between the nub and bone plate, and the adjacent vertebral bodies do not align in a co-planar manner. In some embodiments thereof, the first angle $\alpha$ differs from second angle $\beta$ by at least 5 degrees.

Figure 11:
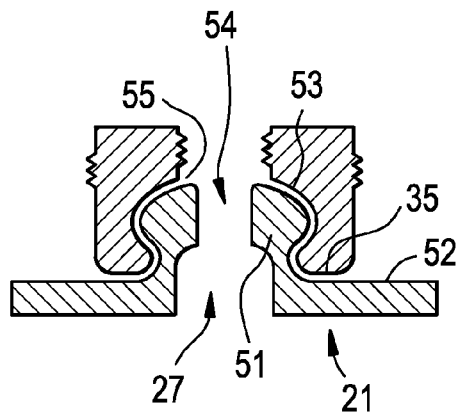
FIG. 11 discloses a cross-section view of a second embodiment of a polyaxial assembly of the present invention.
Figure 16:
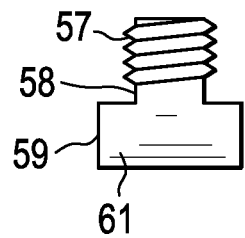
FIG. 16 discloses a threaded post of the present invention.

In a second polyaxial preferred embodiment, and now referring to FIG. 11, the plate has an annular projection 51 extending distally from its inner surface 52 about the central hole, and the nub has a recessed surface 53 extending distally about its throughhole 54 from its second wall, so that the annular projection forms a polyaxial joint 55 with the recessed surface of the nub. The polyaxial nature of the connection between the plate and nub allows the plate to float over the nub. This ability to float facilitates the plate's fit upon vertebral body sidewall surfaces that are often not aligned in a coplanar manner. A post may be added to the assembly by passing it through the plate's central hole and attaching to the nub's throughhole. Now referring to FIG. 16, a thread 57 on the post's shaft 58 allows it to threadably mate with the throughhole of the nub, while a head 59 on the proximal end portion 61 of the post allows it to loosely retain the plate upon the nub. Thus the post acts to retain the plate on the nub while allowing the polyaxial connection to retain its ability to move. Once the desired angulation is achieved, the post may be further tightened upon the assembly to lock the desired angulation.

It is believed that the device of FIG. 11 represents the first polyaxial plate known to the present inventors.

Therefore, in accordance with the present invention, there is provided an interbody device for fusing a disc space, comprising:
a) a bone plate comprising a bone contacting inner surface, an outer surface, upper and lower holes, a central hole, each hole passing from the outer surface to the inner surface, and an annular projection extending distally from the inner surface about the central hole,
b) an intervertebral component comprising:
i) a first wall facing the disc space,
ii) a second wall contacting the inner surface of the bone plate,
iii) a throughhole extending from the first wall to the second wall,
iv) a recessed surface extending distally about the throughhole,
c) first and second bone anchors passing through the upper and lower holes of the bone plate, wherein the annular projection of the bone plate forms a polyaxial joint with the recessed surface of the intervertebral component.

In general, the cage of the present invention can be any interbody fusion cage suitable for promoting fusion between two vertebral bodies. The cage can be adapted for lumbar, cervical or thoracic use. The cage can be adapted for lateral, posterior, or anterior insertion. In some preferred embodiments, the cage is adapted for lateral approach to the lumbar spine. Typically, the cage will have an anterior wall, a posterior wall, leading and trailing walls connecting the anterior and posterior walls to form a central vertical throughhole, an upper surface adapted for gripping an upper endplate and a lower surface adapted for gripping a lower endplate. The central vertical throughhole facilitates bone growth between the two adjacent vertebral endplates. Each of the posterior and anterior walls may have ventral-dorsal throughholes 62 therethrough in order to accommodate fusion as well. The leading wall of the lateral cage may have a bulleted nose 63 that eases insertion into the disc space.

The bone plate of the present invention typically comprises a bone-contacting inner surface, an outer surface, and upper and lower holes passing from the bone-contacting surface to the outer surface. Bone anchors pass through these upper and lower holes to thereby anchor the plate to the adjacent vertebral bodies.

In some embodiments, and now referring to FIGS. 7, 8, and 10, the central hole of the plate (into which the post seats) opens laterally onto a sidewall 65 of the plate. The purpose of this lateral opening is to allow a snap-fit assembly. It is believed that when this opening constitutes about 40% of the central hole periphery, the snap fit will be sufficiently robust so as to hold plate on the post.

In some embodiments, the central hole in the plate is provided in the form of an elongated slot. The elongated slot allows for slidable adjustment of the plate upon the nub, thereby allowing for a fine tuning of the plate location after the nub location is set.

In some embodiments, the bone-contacting inner surface of the plate narrows distally. This contouring helps the plate fit between the adjacent vertebrae. This feature is believed to be advantageous in MIS procedures in which the components are inserted into the spinal area through a tube in the absence of a clear line of sight on the part of the surgeon.

Figure 13:
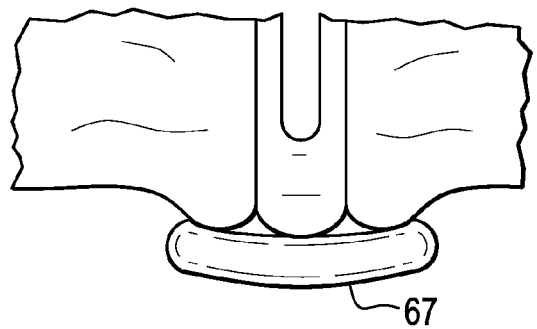
FIG. 13 shows a side view of a concave bone plate attached to both sidewalls of adjacent vertebral bodies.
Figure 14:
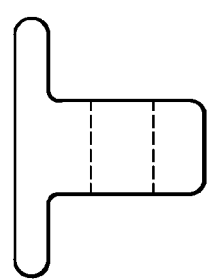
FIG. 14 discloses a side view of a conventional fusion device comprising an integral cage and plate.

In some embodiments, as in FIG. 13, the outer surface 67 of the bone plate is convex. This condition helps the plate conform to the convex bony surfaces of the adjacent vertebrae.

Figure 12:
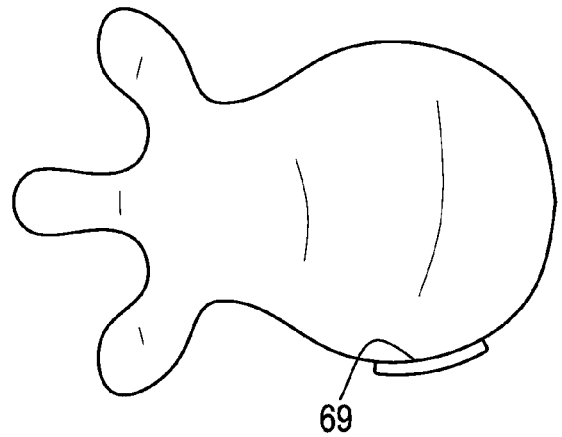
FIG. 12 shows a top view of a concave bone plate attached to a sidewall of a vertebral body.

In some embodiments, as in FIG. 12, the bone-contacting inner surface 69 of the bone plate is concave. This condition helps the plate conform to the convex bony surfaces of the adjacent vertebrae.

Figure 3:
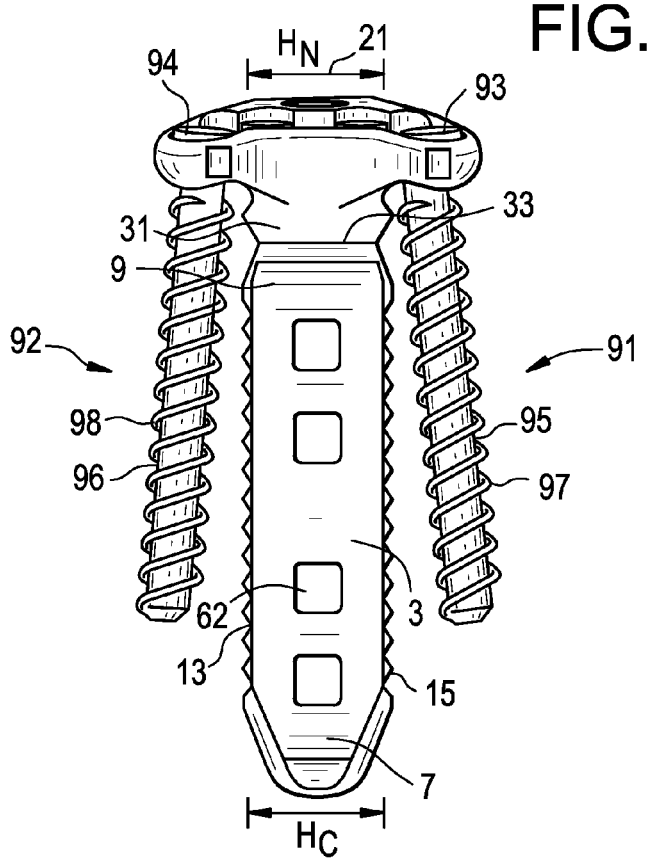
FIG. 3 shows a front view of a device of the present invention.
Figure 4:
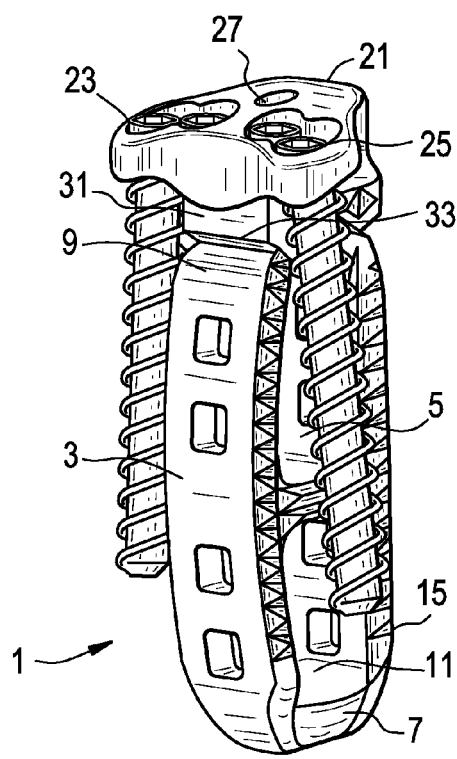
FIG. 4 shows a perspective view of a device of the present invention.

In some embodiments, as in FIG. 3, the inner surface of the plate further comprises a radius 201 and a projection 203. This radius advantageously matches the contour of the vertebral body in this region.

As discussed above, the purpose of the nub is to prevent undesired pivoting of the plate about its centerpoint.

In some embodiments, the cage, plate and nub are present as separate components. This condition maximizes the surgeon's ability to adjust the location of the plate after fixing the locations of the cage and nub.

Figure 15:
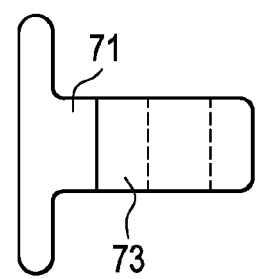
FIG. 15 is a side view of a device of the present invention in which the nub and plate are integral.

In some embodiments, and now referring to FIG. 15, the nub and plate are an integral component 71 that is separate from the cage 73.

Therefore, in accordance with the present invention, there is provided an intervertebral fusion device comprising:
 a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate,
 b) a separate bone plate component comprising a bone contacting surface, and outer surface, upper and lower holes passing from the bone-contacting surface to the outer surface, and a projection extending distally from the bone contacting surface,
 wherein the projection of the bone plate contacts the trailing wall of the cage.

In some embodiments, and now referring to FIGS. 7 and 8, the nub further comprises:
 iii) an upper surface adapted for gripping an upper endplate, and
 iv) a lower surface adapted for gripping a lower endplate
wherein each of the upper and lower surfaces of the nub is disposed between the first and second walls of the nub.

In preferred embodiments, gripping is accomplished by providing a plurality of teeth 75 upon each of the upper and lower surfaces. The purpose of these nub teeth is to enhance the snug fit of the nub between the vertebral bodies and thereby further prevent the rocking of the plate.

In some embodiments, and now referring to FIG. 3, the upper surface and lower surface of the cage define a cage height, and the lower surface and upper surface of the nub define a nub height, and wherein the nub height $H_N$ is not greater than the cage height $H_C$. This condition enhances the ability of the surgeon to transport the nub down the same MIS tube as the cage.

In some embodiments, the nub height is not less than the cage height. This condition enhances the snug fit of the nub between the vertebral bodies and thereby further prevent the rocking of the plate.

In some embodiments, the nub height is substantially the same as the cage height. This condition possess the attributes of the two conditions described above.

In some embodiments, and now referring to FIG. 3, the nub narrows distally. This contouring helps the nub locate the hole in the annulus through which the cage has been placed. This feature is believed to be advantageous in MIS procedures in which the components are inserted into the spinal area through a tube without the surgeon having a clear line of sight.

Figure 17:
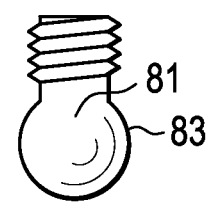
FIG. 17 discloses a post of the present invention having a spherical head.
Figure 18:
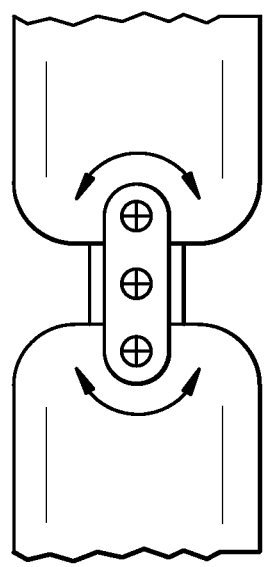
FIG. 18 discloses a side view of a conventional cage-plate assembly inserted in a disc space.

The function of the post is to retain the plate on the nub. Typically, and now referring to FIGS. 16 and 17, the post has a threaded distal end portion adapted for threadable mating to the central hole of the nub. In some embodiments, the post has a proximal end portion forming an enlarged head. In some embodiments thereof, the proximal head 81 has a spherical portion 83.

Typically, the post passes through the central hole of the plate and threads into the nub. However, in some embodiments, the post can thread into the cage as well.

Generally, and now referring to FIGS. 3 and 9, the device of the present invention also comprises upper and lower bone anchors 91,92 received in the respective upper and lower holes, each bone anchor having a proximal head 93,94 and a distal shaft 95,96. Preferably, the bone anchor is a screw that has a threaded shaft 97,98.

Figure 5:
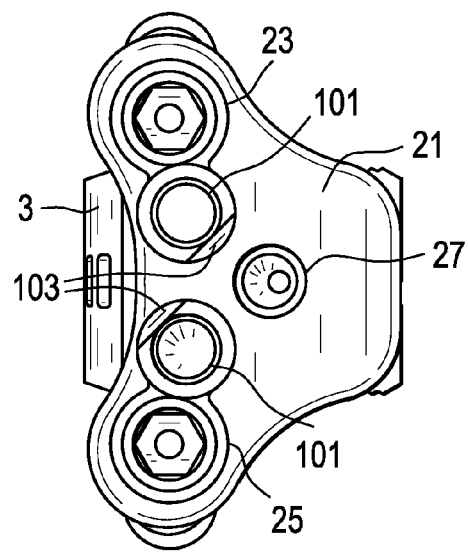
FIG. 5 shows a side view of a device of the present invention.
Figure 6:
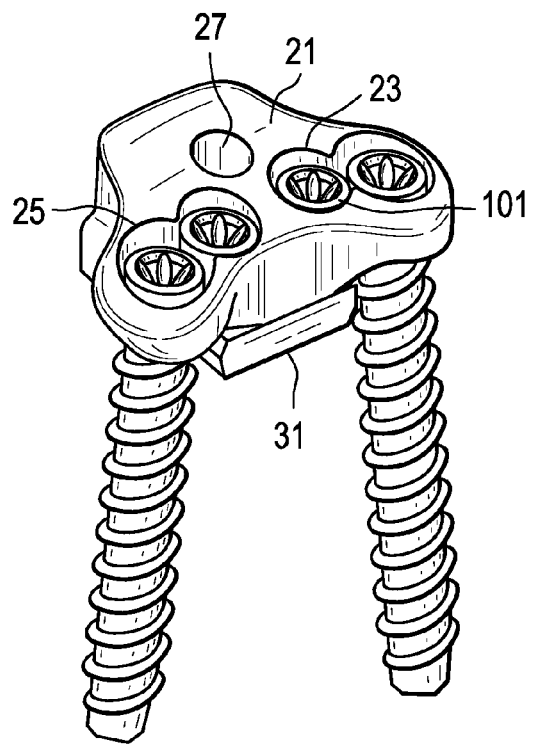
FIG. 6 shows a perspective view of a device of the present invention without its cage.

Generally, and now referring to FIGS. 5 and 6, the device of the present invention also comprises first and second cams 101 threadably received in the respective threaded recesses 103 of the bone plate and bearing against the respective heads of the bone anchors. These cams tighten against the heads of the screws, thereby preventing screw backout.

The cages of the present invention may be made from any non-resorbable material appropriate for human surgical implantation, including but not limited to, surgically appropriate metals, and non-metallic materials, such as carbon fiber composites, polymers and ceramics.

The interbody devices are preferably made out of PEEK or CFRP or any other suitable material providing adequate strength and radiolucency. However, implantable metals such as titanium or stainless steel components may be required to ensure adequate strength for either the interbody device. In some cases the interbody device can be made as a combination of PEEK and metal. In some cases, resorbable materials such as polylactide, polyglycolide, and magnesium are preferred.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany.

In some embodiments, the cage member comprises PEEK. In others, it is a ceramic.

In some embodiments, the first component consists essentially of a metallic material, preferably a titanium alloy or a chrome-cobalt alloy.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
40-99% (more preferably, 60-80 vol %) polyarylethyl ketone (PAEK), and
1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

In some embodiments, the post and screw components of the present invention are made from a biocompatible metal, such as stainless steel, chromium cobalt, or titanium alloy.

In some embodiments, the plates of the present invention are made from a biocompatible metal, such as stainless steel, chromium cobalt, or titanium alloy.

Although the present invention has been described with reference to its preferred embodiments, those skillful in the art will recognize changes that may be made in form and structure which do not depart from the spirit of the invention.

In some embodiments, the central throughhole of the cage is filled with a fusion material. This fusion material promotes bony fusion of the adjacent vertebral bodies through the disc space. In some embodiments, the fusion material may be autograft bone marrow or allograft bone. In some embodiments, the fusion material may be synthetic, such as tricalcium phosphate or hydroxyapatite. In some embodiments, the fusion material may be a recombinant protein, such as a growth factor.

Implant Placement without a Plate Cage Connection

After successfully accessing, clearing and sizing the disc space, select the corresponding implant, fill the cage implant with autogenous bone graft material and attach to the inserter. Gently impact the cage implant into the disc space while monitoring placement under AP fluoroscopy. Ideal placement of the implant is to support the endplate medial/laterally to the contra-lateral rim and between the anterior third and middle third of the disc space from an anterior/posterior perspective.

Select the appropriate nubbed plate implant based on morphology and cage size, attach it to its respective inserter. Using the cage as a guide, insert the plate until the nubbed portion is within the disc space supporting the vertebral body rim and the plate portion abuts the ipsilateral walls of the superior and inferior vertebral bodies. The nubbed plate can be slightly repositioned from the cage location anteriorly or posteriorly in order to optimize the screw location or to account for anomalies such as osteophytes or a slightly compromised cage trajectory.

Attach the plate with the appropriate anchors.

Implant Placement with the Plate and Cage Connected

After successfully accessing, clearing and sizing the disc space, select the corresponding implant, fill the cage portion with autogenous bone graft material and attach the plate-cage combination to the inserter. Gently impact the implant into the disc space while monitoring placement under AP fluoroscopy. Ideal placement of the implant is for the cage portion to support the endplate medial/laterally to the contra-lateral rim and for the nubbed portion to support the ipsilateral rim while the plate portion is in contact with the walls of the superior and inferior vertebral bodies. The implant should be between the anterior third and middle third of the disc space from an anterior/posterior perspective.

The nubbed plate portion can only be slightly repositioned from the cage based on the extent of the polyaxial/sliding connection between the plate and nubbed portion. This allows for a diminished ability to accommodate morphological or surgical anomalies but increases the ergonomics of the surgery by reducing it to a single insertion technique.

Attach the plate with the appropriate anchors.

In some embodiments, the nub supports the ipsilateral rim of the vertebral body and the cage supports the contralateral rim of the vertebral body.

We claim:

1. An intervertebral fusion device comprising:
    a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate;
    b) a bone plate comprising a bone contacting surface, an inner surface, an outer surface, a plurality of sidewalls, upper and lower holes, and a central hole that opens laterally to at least one of the plurality of sidewalls,
    c) a separate nub component interposed between the inner surface of the bone plate and the trailing wall of the cage, the separate nub component comprising a first wall facing the trailing wall of the cage and a second wall facing the inner surface of the bone plate, and a post extending from the second wall and wherein the post is disposed in the central hole that opens laterally;
    wherein the inner surface of the bone plate is concave and the second wall of the separate nub is convex to provide tilting of the plate with respect to the nub component.

2. The device of claim 1 further comprising:
    a) upper and lower bone anchors received in the respective upper and lower screw holes, each bone anchor having a proximal head and a shaft.

3. The device of claim 2 wherein each bone anchor is a bone screw, and the upper and lower holes in the bone plate are screw holes.

4. The device of claim 2 wherein the bone plate has first and second threaded recesses adjoining the respective upper and lower holes.

5. The device of claim 4 further comprising
    a) first and second cams threadably received in the respective threaded recesses of the bone plate and bearing against the respective heads of the bone anchors.

6. The device of claim 2 wherein the shaft of the upper bone anchor and the upper surface of the cage define a first angle $\alpha$, wherein the shaft of the lower bone anchor and the lower surface of the cage define a second angle $\beta$, and wherein the first angle $\alpha$ is not equal to the second angle $\beta$.

7. The device of claim 1 wherein the nub comprises:
    a) a first wall contacting the trailing wall of the cage,
    b) a second wall contacting the bone plate,
    c) a threaded recess extending from the first wall to the second wall, and wherein the post comprises a threaded post received in the threaded recess of the nub and passing through the hole of the bone plate.

8. The device of claim 7 wherein the threaded post has a proximal head, and wherein the proximal head of the threaded post and the hole of the bone plate form a polyaxial joint.

9. The device of claim 1 wherein the nub comprises:
a) a first wall contacting the trailing wall of the cage,
b) a second wall contacting the bone plate,
c) an upper surface adapted for gripping an upper endplate, and
d) a lower surface adapted for gripping a lower endplate
wherein each of the upper and lower surfaces of the nub is disposed between the first and second walls of the nub.

10. The device of claim 9 wherein the upper surface and lower surface of the cage define a cage height, wherein the lower surface and upper surface of the nub define a nub height, and wherein the nub height is substantially the same as the cage height.

11. The device of claim 1 wherein the leading wall of the cage has a rounded nose.

12. The device of claim 1 wherein the post snap fits in the hole that opens laterally.

13. The device of claim 1 wherein the post is generally cylindrically shaped.

14. The device of claim 13 wherein the post has a cylindrically shaped lateral outer portion.

15. The device of claim 1 wherein the post has a generally cylindrically shaped lateral outer portion, the central hole of the plate has a wall that is generally cylindrically shaped, and the outer portion of the post contact the wall of the central hole of the plate.

16. A method of performing surgery on a functional spinal unit comprising an intervertebral space and opposing vertebral bodies, comprising the steps of:
a) inserting the cage of the device of claim 1 into the disc space, and
b) fixing the plate of the device of claim 1 on the opposing vertebral bodies.

17. The method of claim 16 wherein the nub supports an ipsilateral rim of each vertebral body and the cage supports a contralateral rim of each vertebral body.

* * * * *